United States Patent
Yamauchi

(10) Patent No.: US 7,052,496 B2
(45) Date of Patent: May 30, 2006

(54) INSTRUMENT FOR HIGH-FREQUENCY TREATMENT AND METHOD OF HIGH-FREQUENCY TREATMENT

(75) Inventor: Koji Yamauchi, Tokyo (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 10/315,714

(22) Filed: Dec. 10, 2002

(65) Prior Publication Data

US 2003/0109876 A1   Jun. 12, 2003

(30) Foreign Application Priority Data

Dec. 11, 2001   (JP) ............................. 2001-377606
Dec. 11, 2001   (JP) ............................. 2001-377607

(51) Int. Cl.
*A61B 18/18* (2006.01)

(52) U.S. Cl. .......................................... 606/51; 606/49

(58) Field of Classification Search ................ 606/41, 606/45, 50, 52
See application file for complete search history.

(56) References Cited

U.S. PATENT DOCUMENTS

| | | | | |
|---|---|---|---|---|
| 3,920,021 A * | 11/1975 | Hiltebrandt | ................. | 606/50 |
| 4,492,231 A | 1/1985 | Auth | | |
| 5,269,780 A | 12/1993 | Roos | | |
| 5,626,578 A * | 5/1997 | Tihon | ........................ | 606/48 |
| 5,688,270 A | 11/1997 | Yates et al. | | |
| 5,702,390 A | 12/1997 | Austin et al. | | |
| 5,853,412 A | 12/1998 | Mayenberger | | |
| 5,891,142 A * | 4/1999 | Eggers et al. | ................. | 606/51 |
| 6,024,744 A | 2/2000 | Kese et al. | | |
| 6,096,037 A * | 8/2000 | Mulier et al. | ................. | 606/49 |
| 6,152,923 A * | 11/2000 | Ryan | ........................... | 606/51 |
| 6,187,003 B1 | 2/2001 | Buysse et al. | | |
| 6,273,887 B1 | 8/2001 | Yamauchi et al. | | |
| 6,358,249 B1 * | 3/2002 | Chen et al. | ................... | 606/45 |
| 6,416,509 B1 * | 7/2002 | Goble et al. | .................. | 606/37 |
| 6,482,205 B1 * | 11/2002 | Bonnet | ........................ | 606/51 |
| 2001/0037109 A1 | 11/2001 | Yamauchi et al. | | |

FOREIGN PATENT DOCUMENTS

| | | |
|---|---|---|
| DE | 40 32 471 C2 | 4/1992 |
| DE | 41 38 116 A1 | 3/1993 |
| EP | 0 598 348 A1 | 5/1994 |
| JP | 07-171163 | 7/1995 |

(Continued)

OTHER PUBLICATIONS

Japanese Office Action (and English translation) mailed Aug. 13, 2002 which issued in a counterpart Japanese application No. 10-248673 corresponding to U.S. Appl No. 09/884,920.

*Primary Examiner*—Roy D. Gibson
(74) *Attorney, Agent, or Firm*—Frishauf, Holtz, Goodman & Chick, P.C.

(57) ABSTRACT

An instrument for high-frequency treatment is provided which includes a first jaw having, on a first holding surface thereof, an active electrode provided with a substantially flat portion and a protruded portion, and a second jaw having an opposing electrode formed on a second holding surface opposed to the first holding surface. The opposing electrode includes a portion opposed to the protruded portion of the active electrode, and the opposing portion has a shape different from that of the protruded portion of the active electrode. The instrument also includes an operation member for opening and closing the first jaw and the second jaw.

32 Claims, 6 Drawing Sheets

FOREIGN PATENT DOCUMENTS

| | | |
|---|---|---|
| JP | 08-317934 | 12/1996 |
| JP | 08-317936 | 12/1996 |
| JP | 10-199 | 1/1998 |
| JP | 11-155877 | 6/1999 |

\* cited by examiner

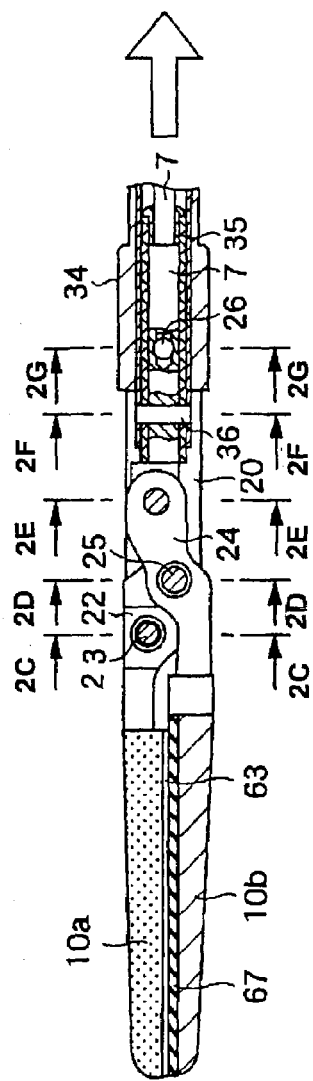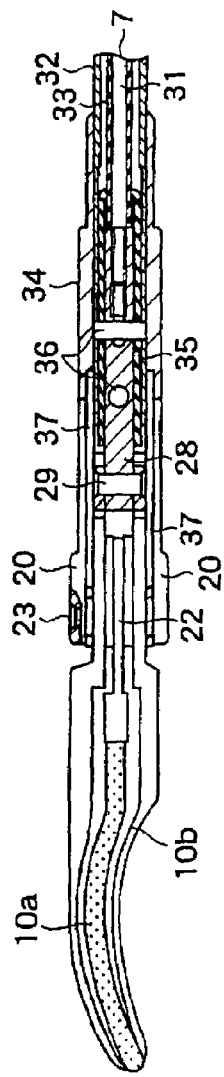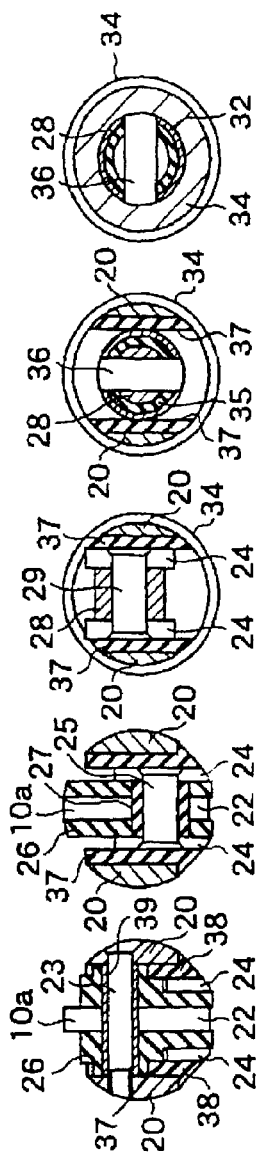

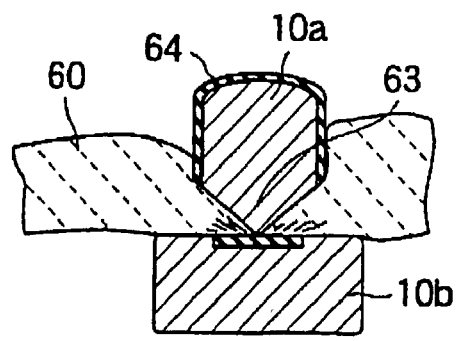 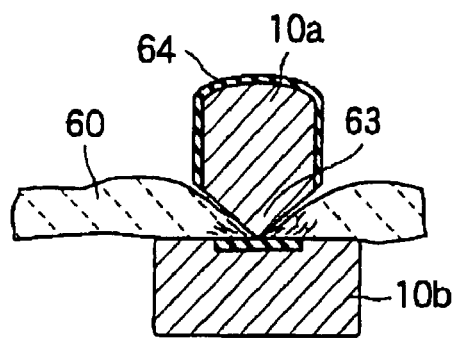
FIG.6A        FIG.6B
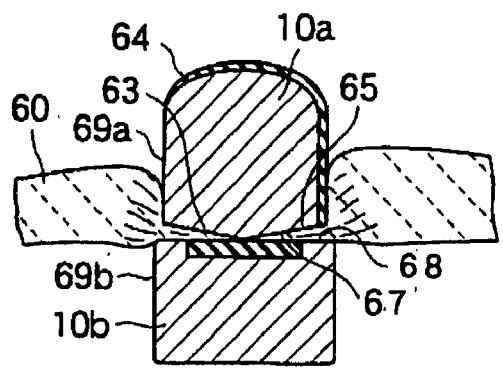
FIG.7
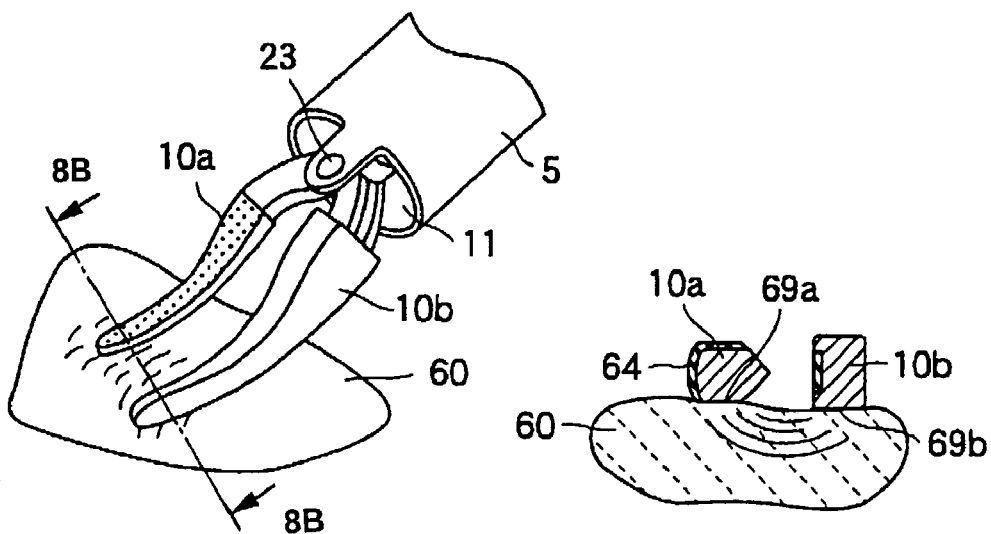
FIG.8A        FIG.8B

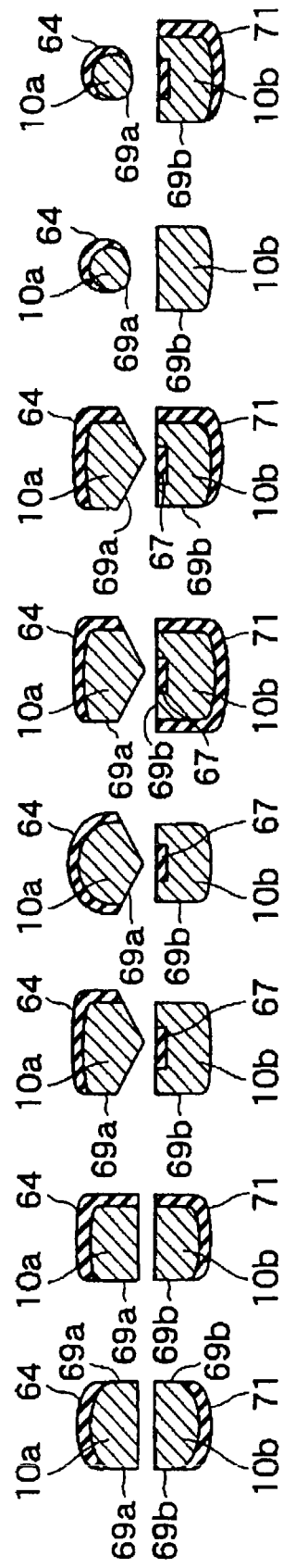

INSTRUMENT FOR HIGH-FREQUENCY TREATMENT AND METHOD OF HIGH-FREQUENCY TREATMENT

CROSS-REFERENCE TO RELATED APPLICATION

This application is based upon and claims the benefit of priority from prior Japanese Patent Application No. 2001-377606, filed Dec. 11, 2001, and Japanese Patent Application No. 2001-377607, filed Dec. 11, 2001, the entire contents of which are incorporated herein by reference.

BACKGROUND OF THE INVENTION

1. Field of the Invention

This invention relates to an instrument for high-frequency treatment and a method of high-frequency treatment by utilizing high-frequency energy. More particularly, the invention relates to an instrument for high-frequency treatment and a method of high-frequency treatment useful for surgical operations using an endoscope.

2. Description of the Related Art

A treating instrument for surgical operations using an endoscope can be an instrument for high-frequency treatment that cuts or coagulates living body tissues by using high frequencies. This kind of instrument for high-frequency treatment is equipped with a pair of jaws each of which is provided with an electrode for feeding a high-frequency current. The pair of jaws holding the living body tissue for effecting a desired treatment with high-frequency energy are called bipolar forceps. Bipolar forceps have heretofore been used for arresting the bleeding of blood vessels and for closing Fallopian tubes, i.e., for coagulating living body tissue that is to be treated or for cutting living body tissue that has been coagulated.

A conventional bipolar forceps have been disclosed in JP-A-10-199. This bipolar forceps include a first electrode member that turns about an axis and a second electrode member opposed thereto. The first electrode member has, separately from each other, a cutting electrode surface with a cutting edge formed on the peripheral surface about the axis thereof and a coagulating electrode surface having a wide area. To use the bipolar forceps, either the cutting electrode surface or the coagulating electrode surface is selected by turning the first electrode member about its axis so as to direct the selected electrode surface to the second electrode. Therefore, either one of the electrode surfaces to be used must be selected depending upon whether tissue is to be cut or coagulated.

As bipolar forceps of another type, there has also been known bipolar forceps in which the tissue-holding portion of the pair of jaws is divided into a front region and a rear region, i.e., into a cutting portion for cutting the tissue and a holding portion for coagulating the tissue. In the bipolar forceps of this type, the cutting and the coagulation are effected separately at different places of the jaws.

The former bipolar forceps are capable of effecting both treatments, i.e., cutting and coagulation without changing the instrument. Depending upon cutting the tissue or coagulating the tissue, however, skill is necessary for changing the direction by turning the first electrode member about its axis.

In the latter bipolar forceps, the part for cutting the tissue and the part for coagulating the tissue are separated functionally and completely. Therefore, depending upon whether tissue is to be cut or coagulated, the operation for holding the tissue must be effected again.

The conventional bipolar forceps are capable of executing both of cutting and coagulation treatments. When the tissue is to be coagulated, however, the tissue must be held by the pair of electrode members, and a high-frequency current must be fed into the held tissue. Therefore, the held tissue could be coagulated only locally.

BRIEF SUMMARY OF THE INVENTION

This invention provides an instrument for high-frequency treatment comprising a first jaw having, on a first holding surface thereof, an active electrode provided with a substantially flat portion and a protruded portion, and a second jaw having an opposing electrode formed on a second holding surface opposed to the first holding surface. The opposing electrode has a portion opposed to the protruded portion of the active electrode, and the opposing electrode has a shape different from that of the protruded portion of the active electrode. The instrument also includes an operation member for opening and closing the first jaw and the second jaw.

BRIEF DESCRIPTION OF THE DRAWINGS

These and other features, and advantages of the instruments and methods of the present invention will become better understood based on the following description, appended claims, and accompanying drawings wherein:

FIGS. 2A and 2B are vertical sectional views of an end portion of the instrument for high-frequency treatment, FIG. 2C is a sectional view along the line 2C—2C in FIG. 2A, FIG. 2D is a sectional view along the line 2D—2D in FIG. 2A, FIG. 2E is a sectional view along the line 2E—2E in FIG. 2A, FIG. 2F is a sectional view along the line 2F—2F in FIG. 2A, and FIG. 2G is a sectional view along the line 2G—2G in FIG. 2A;

FIGS. 6A and 6B are lateral sectional views taken near a proximal end portion of the treating portion in a state where the instrument for high-frequency treatment is used;

FIG. 7 is a lateral sectional view near a front end portion of the treating portion in a state where the instrument for high-frequency treatment is used;

FIGS. 8A and 8B are views illustrating another state of using the instrument for high-frequency treatment;

FIGS. 10A, 10B, 10C, 10D, 10E, 10F, 10G and 10H are vertical sectional views illustrating various modified examples of an upper jaw provided with an exposed electrode and of a lower jaw opposed thereto.

DETAILED DESCRIPTION OF THE EXAMPLES OF THE INVENTION

Figures 1A, 1B, 1C:
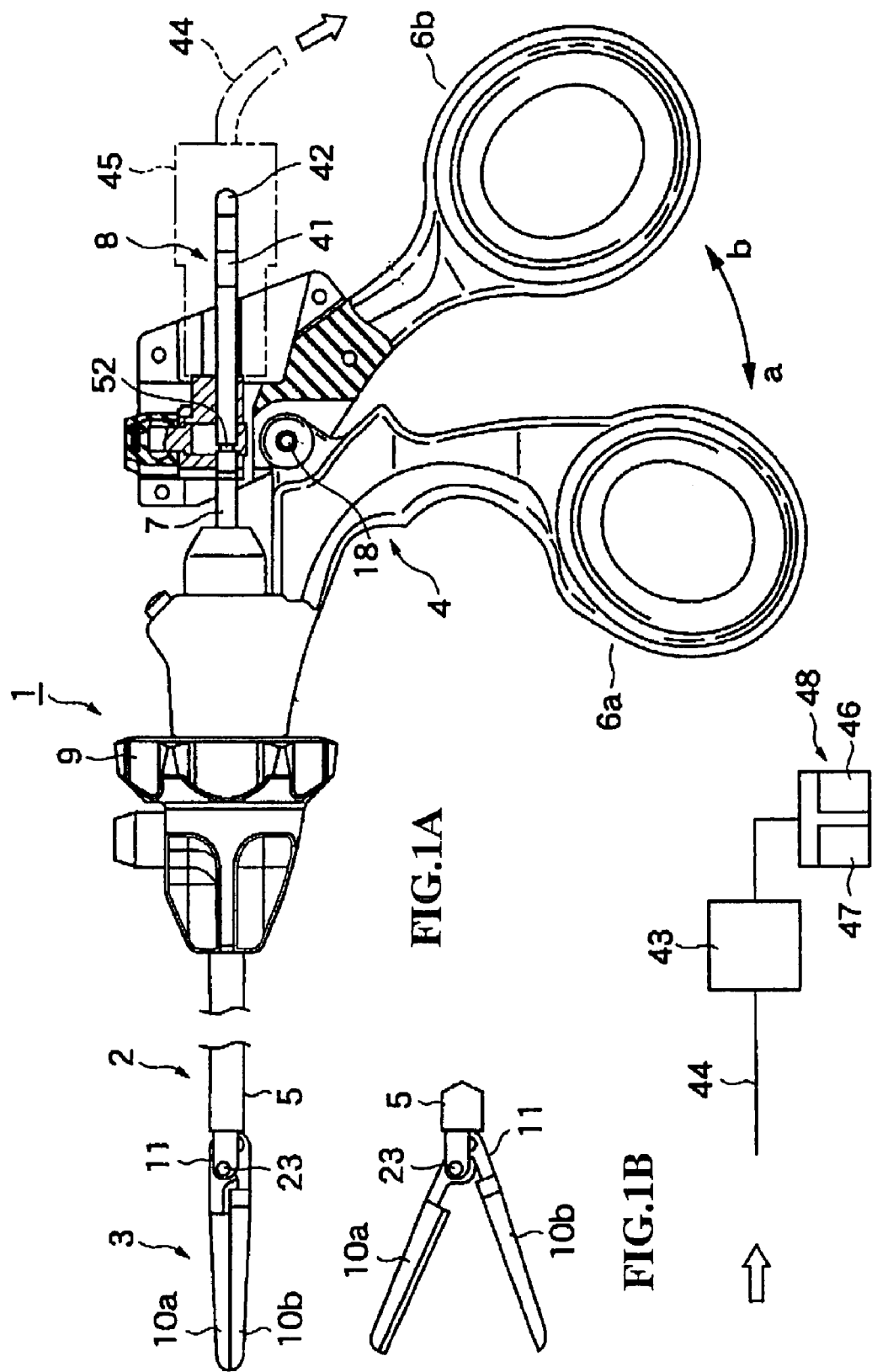
FIGS. 1A, 1B and 1C illustrate a first embodiment of the invention, FIG. 1A being a diagram illustrating a whole instrument for high-frequency treatment, FIG. 1B being a side view of a treating portion of the instrument for high-frequency treatment, and FIG. 1C being a diagram illustrating a power source device for high-frequency cauterization.
Figure 3:
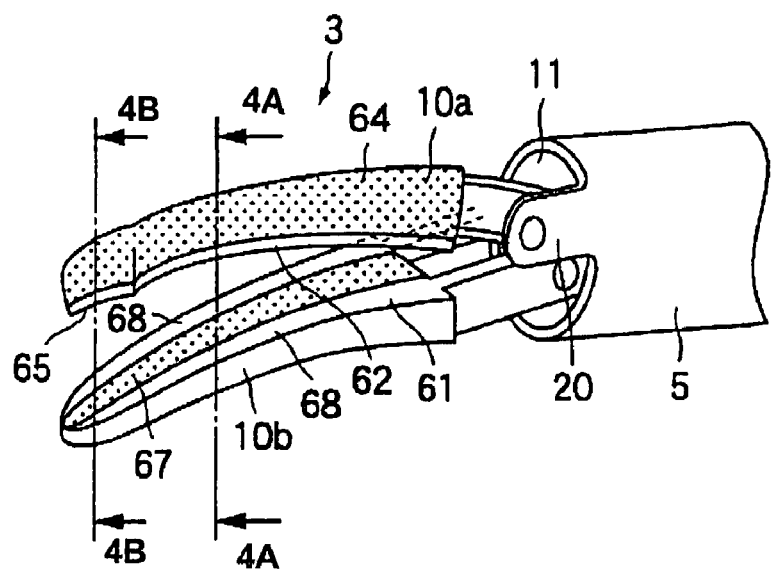
FIG. 3 is a perspective view in a state where the treating portion of the instrument for high-frequency treatment is opened.

An instrument for high-frequency treatment according to one embodiment of the invention will now be described with reference to the drawings. The instrument for high-frequency treatment according to this embodiment is constituted as bipolar forceps 1. The bipolar forceps 1 include a slender insertion portion 2 inserted in the body cavity of a patient, a treating portion 3 arranged at a front end portion of the insertion portion 2 for effecting such a treatment as coagulation or cutting by holding living body tissue (at surgical site in a patient), and an operation portion 4 coupled to a proximal end portion of the insertion portion 2.

The operation portion 4 is provided with a fixed handle 6a and a trigger handle 6b. Upon turning the trigger handle 6b, the treating portion 3 is opened and closed. The treating portion 3 is coupled to an end of a rod (shaft) 7 that incorporates an electrically conducting member, and is assembled integrally with the rod 7 to thereby constitute a treating instrument unit 8. The insertion portion 2 is provided with a sheath 5 that is allowed to freely rotate, and the rod 7 is arranged in the sheath 5 so as to protrude and retract. The proximal end of the sheath 5 is provided with a rotary operation knob 9. By using the rotary operation knob 9, the insertion portion 2 and the treating instrument unit 8 incorporated therein can be rotated integrally together.

A pair of jaws 10a, 10a constituting the treating portion 3 are coupled to the end of the rod 7 of the treating instrument unit 8 via a link mechanism 11. The pair of jaws 10a, 10b work as a holding member for holding living body tissue between the opposing holding surfaces, and include electrodes for feeding a high-frequency current to the held living body tissue. In this embodiment, the jaws are formed of electrically conducting integral members such as a metal.

As shown in FIGS. 2A–2G, the pair of jaws 10a, 10b constituting the treating portion 3 of the bipolar forceps 1 are pivoted by a pair of right and left support arms 20 which are so provided as to protrude from the end of the sheath 5, and the proximal end portions thereof are coupled to the front end of the rod 7 through the link mechanism 11. That is, referring to FIG. 2C, a proximal end portion 22 of the upper jaw 10a is directly pivoted to the pair of right and left support arms 20 through a pivot pin 23. As shown in FIG. 2D, a proximal end portion 24 of the lower jaw 10b is branched into two, and the proximal end portion 22 of the upper jaw 10a is sandwiched therebetween. The proximal end portions 22 and 24 are pivoted by a pivot pin 25 spanning across them. Further, an electrically insulating protection tube 27 is fitted onto the pivot pin 25, and is further fitted into the proximal end portion 22 of the upper jaw 10a to electrically insulate the upper jaw 10a and the lower jaw 10b from each other. The two proximal end portions 22 and 24 are further electrically insulated even by using an insulating spacer 26. As shown in FIG. 2E, front end portions of a connection member 28 coupled to an end of the rod 7 is fitted to the branched two proximal end portions of the lower jaws 10b, and the two proximal end portions 24 are pivoted by a pivot pin 29. As shown in FIG. 2B, further, a front end of an inner shaft 31 in the rod 7 is screwed into the rear end of the connection member 28, whereby the connection member 28 is coupled to the inner shaft 31 of the rod 7, and is electrically connected to the inner shaft 31.

The rod 7 has a metallic outer pipe 32 like the metallic inner shaft 31, and the inner shaft 31 is inserted in the outer pipe 32. An insulating tube 33 of a resin is fitted onto the outer periphery of the inner shaft 31 so as to be interposed between the inner shaft 31 and the outer pipe 32 (i.e., the inner shaft 31 and the outer pipe 32 are electrically insulated from each other). A cylindrical metallic end cover 34 forming the pair of right and left support arms 20 is fitted onto the front end of the outer pipe 32 in a fixed manner. The end cover 34 is further electrically connected to the outer pipe 32.

As shown in FIGS. 2B, 2F and 2G, further, the outer peripheral portion of the connection member 28 is covered with a separate insulating cover 35, which electrically insulates the connection member 28 from the front end cover 34 and from the support arms 20. An electrically insulating pin 36 is buried in the connection member 28 covered with the insulating cover 35.

The inner shaft 31 of the rod 7 is electrically insulated from the outer pipe 32 but is electrically connected to the lower jaw 10b. The outer pipe 32 is electrically connected to the upper jaw 10a. To maintain this wiring, the front end of the inner shaft 31 of the rod 7 is connected to the rear end of the connection member 28, which is connected to the lower jaw 10b directly or through a pin 29. The connection member 28 and the pin 29 are electrically insulated by the insulating cover 37 from the support arms 20 of the front end cover 34. The insulating cover 37 is adhered onto the inner surfaces of the support arms 20. The insulating cover 37 fully extends to the upper and lower sides of the support arms 20 and, particularly, the lower end portion 38 thereof is bent as shown in FIG. 2C so as to arrive at the outer surfaces of the support arms 20, so that the distance along the insulating surface is extended as long as possible. Therefore, the insulating cover 37 exhibits an enhanced electrically insulating effect. A protection pipe 39 is fitted onto the pivot pin 23 and is arranged spanning over the whole bearing pivot member.

The inner shaft 31 of the rod 7 is electrically connected from the connection member 28 to the lower jaw 10b directly or through the pivot pin 29, and the outer pipe 32 is electrically connected from the front end cover 34 to the upper jaw 10a through the pair of right and left support arms 20 and the pivot pin 23, with the two electrically conducting passages being electrically isolated from each other by an insulating member such as the insulating tube 33 or the like.

As shown in FIG. 1A, the rod 7 of the treating instrument unit 8 extends backward from the insertion portion 2 toward the back of the operation portion 4 penetrating through the operation portion 4, and its rear end is protruding outward. The rear end of the rod 7 is provided with a first connection terminal member 41 and a second connection terminal member 42 which are connected separately and electrically to the upper jaw 10a and to the lower jaw 10b. A connector 45 of a cable 44 extending from a power source unit 43 for high-frequency cauterization is fitted to the rear end of the rod 7, so that a current of a high frequency can be fed into the treating portion 3. As shown in FIG. 1C, the power source unit 43 for cauterization is provided with a foot switch 48 having a cutting pedal 46 and a coagulation pedal 47. The cutting pedal 46 is operated to control the power source device 43 for high-frequency cauterization to thereby supply a high-frequency current suitable for the cutting. Further, the coagulation pedal 47 is operated to control the power source device 43 for high-frequency cauterization to thereby supply a high-frequency current suitable for the coagulation. It is further allowed to turn on or off the circuit for feeding electric power to the treating portion 3.

The operation portion 4 incorporates a mechanism in which, the outer pipe 32 of the rod 7 engages with an engaging portion formed in the insertion portion 2 when the treating instrument unit 8 is mounted on the insertion portion 2. Therefore, the treating instrument unit 8 and the insertion portion 2 engage with each other so as to rotate integrally. Further, a groove 52 is formed at an intermediate portion of the front end of the outer pipe 32 of the rod 7 for engaging with a trigger handle 6*b* of the operation portion 4. Upon turning the trigger handle 6*b* about a pivot pin 18 in a direction a–b shown in FIG. 1A, the rod 7 can be moved back and forth. As the rod 7 moves back and forth along the longitudinal axis thereof, the jaws 10*a* and 10*b* turn being operated by the link mechanism 11, and the portions thereof on the front end side undergo opening and closing operations. That is, the treating portion 3 can be operated in a closed state shown in FIG. 1A and an opened state shown in FIG. 1B.

Next, described below with reference to FIGS. 2A to 5 is the constitution of the jaws 10*a*, 10*b* constituting the treating portion 3. The upper and lower jaws 10*a* and 10*b* are made of an electrically conducting material, e.g., metallic members. As shown in FIG. 2B, the upper and lower jaws 10*a* and 10*b* are both formed to be curved toward the right side as viewed from the upper side.

Figure 4A:
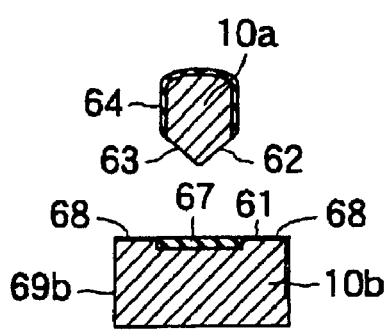
FIG. 4A is a lateral sectional view of the treating portion along the line 4A—4A in FIG. 3 in a state where the instrument for high-frequency treatment is opened.

As shown in FIG. 4A, the holding surface 61 of the lower jaw 10*b* is formed planar and flat over the full length thereof, and the width of the holding surface 61 (thickness in the direction perpendicular to the rotational direction of the jaw) is broad on the proximal end side and is gradually expanding toward the right and left as compared to the width on the front end side. The upper jaw a has 10*a* has transverse width which is narrower over the full length thereof than the width of the lower jaw 10*b* but is in agreement at the front end portion thereof with the width of the lower jaw 10*b*. The upper and lower jaws 10*a* and 10*b* have widths which are generally decreasing toward the front. It is further desired that the upper and lower jaws 10*a* and 10*b* have heights that decrease toward the front end side.

As also shown in FIG. 4A, the holding surface 62 of the upper jaw 10*a* protrudes like a wedge to form a double-edged active electrode portion 63. The active electrode portion 63 protrudes in such a manner that the tip edge thereof is in the form of a ridge continuing along the back-and-forth lengthwise direction of the jaw 10*a*. The active electrode portion 63 has a triangular shape in lateral cross section but may be of a trapezoidal shape or a circular shape.

The summit of the upper jaw 10*a* is formed in a semi-arcuate shape in cross section. An insulating layer material 64 is formed to cover the whole outer surface of the upper jaw 10*a* except the active electrode portion 63 so as to electrically insulate the outer surface. The outer surface may be electrically conductive provided that it is electrically insulated from the active electrode portion 63. The insulating layer material 64 is formed by, for example, being coated with alumina. Namely, the outer periphery of the upper jaw 10*a* is electrically insulated except the active electrode portion 63 formed on the holding surface 62. When an exposed electrode portion 69 that will be described later is provided, however, such a portion is an exception.

Figure 4B:
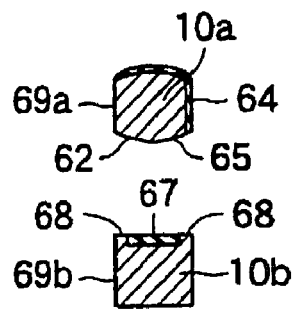
FIG. 4B is a lateral sectional view of the treating portion along the line 4B—4B in FIG. 3 in a state where the instrument for high-frequency treatment is opened.

An end portion of the active electrode portion 63 formed by the holding surface 62 of the upper jaw 10*a* serves as a flat electrode portion 65 formed nearly flat. The flat electrode portion 65 need not be perfectly flat but may be, for example, a swollen portion forming a surface having a gentler inclination than the inclination of protrusion of the active electrode portion 63. FIG. 4B illustrates a shape in cross section of a real flat electrode portion 65 which slightly protrudes at the center thereof to form a mountain shape. Even with this shape, there is obtained the electrode portion 65 which is substantially flat in a functional sense.

The holding surface 61 of the lower jaw 10*b* is provided with an insulating portion 67 formed like a layer by being coated with alumina or the like in the back-and-forth direction over the full length of the central region opposed to the active electrode portion 63 of the upper jaw 10*a*. When the upper and lower jaws 10*a* and 10*b* are closed, the insulating portion 67 prevents the two jaws 10*a* and 10*b* from being short-circuited. Therefore, a pair of right and left exposed portions of the holding surface 61 of the lower jaw 10*b* on both sides of the insulating portion 67, serve as passive electrode portions 68. An insulating layer material (not shown) may also be formed on the outer peripheral surfaces of the lower jaw 10*b* except the holding surface 61.

Figure 5:
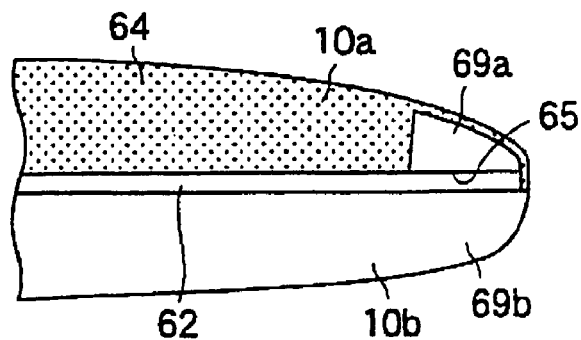
FIG. 5 is a right side view of the treating portion in a state where the instrument for high-frequency treatment is closed.

As shown in FIGS. 4B and 5, an exposed electrode portion 69*a* serving as a first electrode is partly formed on the right side surface at the end of the upper jaw 10*a* by not forming the insulating layer material 64 thereon or by removing the insulating layer material 64. Further, the right side surface of the lower jaw 10*b* forms an exposed electrode portion 69*b* serving as a second electrode thereof. The instrument can be easily used when the exposed electrode portions 69*a* and 69*b* are formed on the side-surfaces of the upper and lower jaws 10*a* and 10*b* on the side where they are curved and protruded. Further, the exposed electrode portion 69*a* of the upper jaw 10*a* may be exposed from the end up to an intermediate portion or up to the proximal end portion.

Next, described below is the mode of operation in using the instrument for high-frequency treatment. First, in the case of cutting the tissue, the tissue 60 may be held in any region between the jaws 10*a* and 10*b* of the treating portion 3. When the treatment is mainly for cutting, the tissue is held in the region of the active electrode portion 63 except the flat electrode portion 65 at the end. Namely, as shown in FIG. 6A, the tissue 60 is held between the jaws 10*a* and 10*b*, and a high-frequency current for cutting is fed thereto. Then, the high-frequency current is fed in a concentrated manner into the tissue 60 from the active electrode portion 63, and the tissue 60 is cut by the high-frequency current flowing through the tissue between the jaws 10*a* and 10*b*. Usually, the coagulation is effected simultaneously with the cutting.

Here, the jaw 10*a* on the side of the active electrode portion 63 has been electrically insulated over the outer periphery thereof by the insulating layer material 64 except the active electrode portion 63. Therefore, the high-frequency current does not leak from a portion except the active electrode portion 63. In the case of a relatively thick tissue 60 such as Fallopian tubes as shown in FIG. 6A, in particular, the tissue 60 comes in contact with the portions except the active electrode portion 63 in addition to the active electrode portion 63. Basically, however, the outer periphery other than the active electrode portion 63 has been electrically insulated. Accordingly, the high-frequency current does not leak to unnecessary regions but is concentrated in the active electrode portion 63 to efficiently cut the tissue 60. On the other hand, a thin or fine tissue 60 can be held by the protruded end portion of the active electrode portion 63 as shown in FIG. 6B. Therefore, the high-frequency current concentrates at the end portion of the active electrode portion 63 to efficiently cut the tissue.

In carrying out this treatment, if a high-frequency current for coagulation is fed between the jaws 10*a* and 10*b* of the treating portion 3 as described above, then the held tissue 60 can be coagulated instead of being cut. Further, because the upper jaw 10*a* has been electrically insulated over the outer peripheral portion thereof by the insulating layer material 64 except the active electrode portion 63, a variety of combinations of treatments of cutting and coagulation can be conducted by controlling the high-frequency current or by adjusting the holding speed. Namely, the tissue 60 held at the same position of the jaws 10a and 10b can be cut or coagulated by the switching operation or by a simple operation such as adjusting the holding speed.

Figure 9:
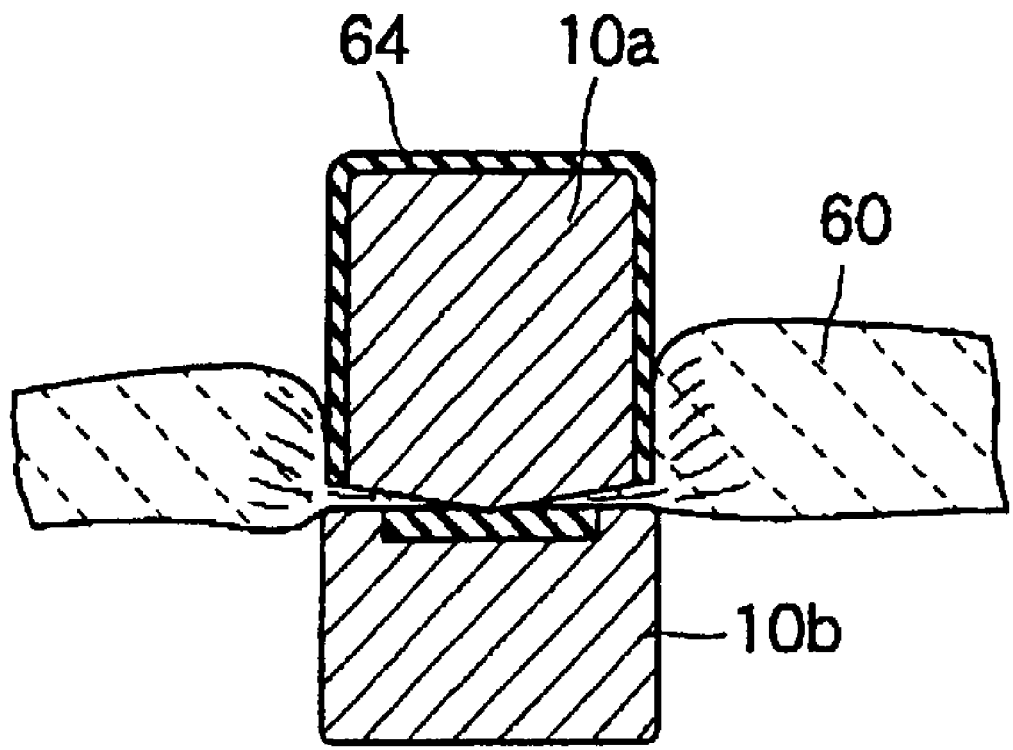
FIG. 9 is a lateral sectional view near the front end portion of the treating portion in a state where the instrument for high-frequency treatment is used.

In conducting the cutting or coagulating operation, it may often be desired to conduct the treatment by heightening the coagulating ability. In this case, the treatment is conducted by holding the tissue 60 at the front end portions of the jaws 10a and 10b. Namely, as shown in FIG. 7, if the tissue 60 is held between the passive electrode portion 68 of the lower jaw 10b and the flat electrode portion 65 in the active electrode portion 63 of the upper jaw 10a, and if a high-frequency current is fed thereto, the treatment such as cutting or coagulation can be conducted by controlling the high-frequency current. The active electrode portion 63 is formed as a nearly flat electrode portion 65, enabling the tissue 60 to be held over a wide area and a high-frequency current to be fed thereto. And because the jaw 10a provided with the active electrode member 63 has been electrically insulated over the outer periphery thereof by the insulating layer material 64 and, hence, the high-frequency current does not leak from a portion except the active electrode portion 63, making it possible to efficiently coagulate the tissue 60. In the case of a relatively thick tissue 60 such as Fallopian tubes as shown in FIG. 7, in particular, the tissue 60 comes in contact with the portions except the active electrode portion 63 in addition to the active electrode portion 63. However, the high-frequency current does not leak to unnecessary regions but is concentrated in the active electrode portion 63 to efficiently coagulate the tissue. In the case of this treatment, if no exposed electrode portion 69 is formed on the side surface of the upper jaw 10a as shown in FIG. 9, the tissue can be coagulated more efficiently.

According to the instrument for high-frequency treatment as described above, a treatment such as coagulation and/or cutting for the living body tissue 60 can be quickly conducted without the need of holding the tissue again, resulting in improved operability. In addition, by utilizing the flat electrode portion 65, the treatment can be easily and quickly conducted while enhancing the coagulating ability.

When it is desired to coagulate the tissue over a wide area, the jaws 10a and 10b of the treating portion 3 are opened as shown in FIGS. 8A and 8B, the exposed electrode portion 69a on the side surface at the end of the upper jaw 10a and the exposed electrode portion 69b on the side surface of the lower jaw 10b are brought into contact with the tissue, and a current for coagulation is fed thereto, to thereby coagulate the tissue over a wide area.

FIGS. 10A–10H illustrates modified examples of the upper jaw 10a and the lower jaw 10b opposed thereto. Namely, FIGS. 10A–10H includes vertical sectional views of the pair of jaws 10a and 10b.

More specifically, FIG. 10A illustrates an example in which exposed electrode portions 69a are provided on the right and left side surfaces of the upper jaw 10a, and FIG. 10B illustrates an example in which the exposed electrode portion 69b is left on one side surface of the lower jaw 10b and an insulating layer material 71 is formed on the other outer peripheral surfaces. FIGS. 10C, 10D, 10E and 10F illustrate examples in which the holding electrode portion at the end of the upper jaw 10a is also formed in a protruded manner like the active electrode portion 63, wherein FIG. 10D illustrates an example in which the outer peripheral side portion of the upper jaw 10a is formed in an arcuate shape, and FIG. 10E illustrates an example in which the outer peripheral surfaces of the lower jaw 10b are covered with the insulating layer material 71. In this case, the tissue enters between the inclined electrode surface 69a of the upper jaw 10a and the electrode surface 69b of the lower jaw 10b, and an electric current is fed to the tissue portion.

FIG. 10F illustrates an example in which the lower jaw 10b is constituted in the same manner as that in FIG. 10B. And FIGS. 10G and 10H illustrate examples in which the upper jaw 10a is formed of an electrically conducting member having a round shape in lateral cross section. In FIG. 10H, by the way, the lower jaw 10b is constituted in the same manner as that of FIG. 10B.

It will be obvious to those having skill in the art that many changes may be made in the above-described details of the preferred embodiments of the present invention. The scope of the present invention, therefore, should be determined by the following claims.

What is claimed is:

1. An instrument for high-frequency treatment comprising:
   a first jaw having, on a first holding surface thereof, an active electrode provided with a substantially flat portion and a protruded portion;
   a second jaw having an opposing electrode formed on a second holding surface opposed to the first holding surface; and
   an operation member for opening and closing the first jaw and the second jaw,
   wherein the opposing electrode includes a portion opposed to said protruded portion and said substantially flat portion of the active electrode, and said opposing electrode has a shape different from that of said protruded portion of the active electrode.

2. An instrument for high-frequency treatment according to claim 1, further comprising a power source for selectively supplying at least one of a high-frequency electric current for cutting and a high-frequency electric current for coagulation across the active electrode and the opposing electrode.

3. An instrument for high-frequency treatment according to claim 1, wherein an outer surface of the first jaw, except where the active electrode is provided, is electrically insulated from the active electrode.

4. An instrument for high-frequency treatment according to claim 1, wherein the first jaw and the active electrode are formed together as a unitary structure by using an electrically conducting member, and outer surfaces of the first jaw except where the active electrode is formed are electrically insulated.

5. An instrument for high-frequency treatment according to claim 1, wherein the second holding surface of the second jaw is electrically insulated at a portion which comes into contact with an end of the active electrode when the first and second jaws are closed, in order to prevent short-circuiting between the active electrode and the opposing electrode.

6. An instrument for high-frequency treatment according to claim 1, wherein the substantially flat portion of the active electrode is formed at a portion closer to a distal end of the first jaw than to the protruded portion of the active electrode.

7. An instrument for high-frequency treatment according to claim 1, wherein a length of the protruded portion of the active electrode along a lengthwise direction thereof is longer than a length of the substantially flat portion of the active electrode.

8. An instrument for high-frequency treatment according to claim 7, wherein the length of the protruded portion of the active electrode along the lengthwise direction thereof is longer than three times the length of the substantially flat portion of the active electrode.

9. An instrument for high-frequency treatment according to claim 1, wherein the substantially flat portion of the active electrode comprises a swollen portion which is inclined more mildly than an inclination of the protruded portion of the active electrode.

10. An instrument for high-frequency treatment according to claim 1, wherein the first jaw and the second jaw are provided in an insertion portion that can be inserted into a body.

11. An instrument for high-frequency treatment according to claim 1, wherein the holding surface of the second jaw has a substantially flat shape over a whole length thereof.

12. An instrument for high-frequency treatment according to claim 1, wherein a lateral width of the first jaw is narrower than a lateral width of the second jaw.

13. An instrument for high-frequency treatment according to claim 1, wherein an area of the holding surface of the first jaw is smaller than an area of the holding surface of the second jaw.

14. An instrument for high-frequency treatment according to claim 1, wherein the first jaw and the second jaw have an elongated shape which as a whole becomes narrow toward end portions of the first and second jaws.

15. An instrument for high-frequency treatment according to claim 1, wherein the active electrodes of the first jaw comprises a first electrode portion and the second jaw comprises a second electrode portion that neighbors the opposing electrode, and wherein the first electrode portion and the second electrode portion are on a same side with respect to a plane formed by opening and closing of the first jaw and the second jaw.

16. An instrument for high-frequency treatment comprising:
a first jaw which is selectively supplied with at least one of a high-frequency electric current for cutting and a high-frequency electric current for coagulation, and which has, on a first holding surface thereof, an active electrode provided with a substantially flat portion and a protruded portion, wherein an outer surface of the first jaw, except where the active electrode is formed, is electrically insulated from the active electrode;
a second jaw having a substantially flat opposing electrode formed on a second holding surface opposed to the first holding surface so as to be opposed to the substantially flat portion and the protruded portion of the active electrode, wherein the second jaw is electrically insulated at a portion which comes into contact with an end of the active electrode in order to prevent short-circuiting between the active electrode and the opposing electrode; and
an operation member for opening and closing the first jaw and the second jaw.

17. An instrument for high-frequency treatment comprising:
clamping means for clamping a surgical site, said clamping means having both a portion with a first area that comes in contact with the surgical site and a portion with a second area that comes in contact with the surgical site when the surgical site is clamped, wherein the first area is smaller than the second area, and wherein the portion with the second area is provided on a same side of the clamping means as the portion with the first area and is offset in a lengthwise direction from the portion with the first area;

operation means for opening and closing the clamping means; and
high-frequency current supplying means for selectively supplying at least one of a high-frequency electric current for cutting and a high-frequency electric current for coagulation to the surgical site that is clamped.

18. A method of treating a surgical site in a patient comprising:
selecting one of a protruded portion and a substantially flat portion from an electrode formed on a holding surface of a first jaw;
holding the surgical site between the selected portion and a holding surface of a second jaw having an opposing electrode; and
selectively applying at least one of a high-frequency electric current for cutting and a high-frequency electric current for coagulation across the electrode of the first jaw and the opposing electrode of the second jaw.

19. A method of treating a surgical site of a patient comprising:
selecting one of an end portion having a substantially flat electrode on a holding surface of a first jaw and a portion other than said end portion having a protruded electrode;
holding the surgical site between the selected portion and a holding surface of a second jaw having an opposing electrode;
applying a high-frequency electric current for coagulation when the surgical site is held between the end portion of the first jaw and the holding surface of the second jaw; and
applying a high-frequency electric current for cutting when the surgical site is held between said portion other than the end portion of the first jaw and the holding surface of the second jaw.

20. An instrument for high-frequency treatment according to claim 1, wherein the substantially flat portion and the protruded portion are arranged along a lengthwise direction of the first jaw such that when the first jaw and second jaw are closed, both the substantially flat portion and the protruded portion are adapted to hold a surgical site.

21. An instrument for high-frequency treatment comprising:
a first jaw having, on a first holding surface thereof, an active electrode provided with a substantially flat portion and a protruded portion such that a length of the protruded portion along a lengthwise direction thereof is longer than a length of the substantially flat portion;
a second jaw having an opposing electrode formed on a second holding surface opposed to the first holding surface; and
an operation member for opening and closing the first jaw and the second jaw,
wherein the opposing electrode includes a portion opposed to said protruded portion of the active electrode, and said opposing electrode has a shape different from that of said protruded portion of the active electrode.

22. An instrument for high-frequency treatment according to claim 21, wherein the length of the protruded portion of the active electrode along the lengthwise direction thereof is longer than three times the length of the substantially flat portion of the active electrode.

23. An instrument for high-frequency treatment according to claim 21, wherein the substantially flat portion of the active electrode is formed at a portion closer to a distal end of the first jaw than the protruded portion of the active electrode.

24. An instrument for high-frequency treatment according to claim 21, wherein the substantially flat portion of the active electrode comprises a swollen portion which is inclined more mildly than an inclination of the protruded portion of the active electrode.

25. An instrument for high-frequency treatment according to claim 21, wherein the holding surface of the second jaw has a substantially flat shape over a whole length thereof.

26. An instrument for high-frequency treatment according to claim 21, wherein a lateral width of the first jaw is narrower than a lateral width of the second jaw.

27. An instrument for high-frequency treatment according to claim 21, wherein an area of the holding surface of the first jaw is smaller than an area of the holding surface of the second jaw.

28. An instrument for high-frequency treatment according to claim 21, wherein the first jaw and the second jaw have an elongated shape which as a whole becomes narrow toward end portions of the first and second jaws.

29. An instrument for high-frequency treatment according to claim 21, wherein the active electrode of the first jaw comprises a first electrode portion and the second jaw comprises a second electrode portion that is adjacent to the opposing electrode, and wherein the first electrode portion and the second electrode portion are on a same side with respect to a plane formed by opening and closing of the first jaw and the second jaw.

30. An instrument for high-frequency treatment comprising:
   a first jaw comprising a first holding surface for holding an object, another surface other than the first surface, and a first electrode for supplying high-frequency current provided on at least a part of each of the first holding surface and said another surface;
   a second jaw comprising a second electrode for accepting the high-frequency current supplied from the first electrode, and a second holding surface for holding the object;
   an operation member for opening and closing the first jaw and the second jaw with respect to each other so that the object can be held between the first holding surface and the second holding surface;
   a first insulating member for electrically insulating a predetermined surface of the first jaw, and which is provided such that said at least a part of each of the first holding surface and said another surface function as the first electrode;
   a second insulating member which is provided on the second holding surface such that the first electrode and the second electrode are insulated from each other when the first jaw and the second jaw contact each other in a closing operation.

31. An instrument for high-frequency treatment according to claim 30, wherein the first jaw has a curved shape, and said another surface is provided on a protruded side of the curved shape.

32. An instrument for high-frequency treatment according to claim 30, wherein the high-frequency electric current is a high-frequency electric current for coagulation.

* * * * *